United States Patent [19]

Rinehart et al.

[11] Patent Number: 5,985,876
[45] Date of Patent: Nov. 16, 1999

[54] NUCLEOPHILE SUBSTITUTED ECTEINASCIDINS AND N-OXIDE ECTEINASCIDINS

[76] Inventors: Kenneth L. Rinehart, 1306 S. Carle Ave.; Tong Zhou, 45-5 RAL, 600 S. Mathews Ave., both of Urbana, Ill. 61801

[21] Appl. No.: 09/058,499

[22] Filed: Apr. 10, 1998

Related U.S. Application Data

[60] Provisional application No. 60/043,596, Apr. 15, 1997.
[51] Int. Cl.$^6$ .................. A01N 43/58; C07D 237/26; C07D 241/36
[52] U.S. Cl. .................. 514/250; 544/233; 544/340
[58] Field of Search .................. 514/250; 544/233, 544/340

[56] References Cited

U.S. PATENT DOCUMENTS

| | | | |
|---|---|---|---|
| 4,273,773 | 6/1981 | Demerson et al. | 424/250 |
| 5,089,273 | 2/1992 | Rinehart et al. | 424/520 |
| 5,459,141 | 10/1995 | Vertesy et al. | 514/250 |
| 5,484,717 | 1/1996 | Zaccardi | 435/119 |

OTHER PUBLICATIONS

Sakai et al., "Ecteinascidins: Putative Biosynthetic . . . ", J. Am. Chem. Soc., 1996, vol. 118, pp. 9017–9023.

*Primary Examiner*—Mukund J. Shah
*Assistant Examiner*—Tamthom N. Truong
*Attorney, Agent, or Firm*—Ernest V. Linek; Banner & Witcoff, Ltd.

[57] ABSTRACT

Five new nucleophile substituted ecteinascidin (Et) compounds have been isolated from extracts of *Ecteinascidia turbinata*. These compounds have been purified by chromatographic techniques and their structures and bioactivities have been determined. The five nucleophile substituted Et compounds have been designated herein as Et 802 (1), Et 788 (2), Et 760 (3), Et 858 (4) and Et 815 (5). Also obtained were three new N-oxide ecteinascidin compounds, which have been designated herein as Et 717 (6), Et 775 (7) and Et 789 (8). Some of these newly discovered Et compounds show exceedingly potent cytotoxicity against L1210.

27 Claims, 9 Drawing Sheets

NUCLEOPHILE SUBSTITUTED ECTEINASCIDINS AND N-OXIDE ECTEINASCIDINS

CROSS-REFERENCE TO RELATED APPLICATION

This application claims the benefit of U.S. Provisional Application Ser. No. 60/043,596 filed Apr. 15, 1997, the teachings of which are incorporated herein by reference.

BACKGROUND OF THE INVENTION

Ecteinascidins (Ets), exceedingly potent antitumor agents, first isolated from the marine tunicate *Ecteinascidia turbinata*, especially Et 743, Et 729, Et 736 and Et 722 show significant efficacy in vivo against tumor cell lines including P388 murine leukemia, B16 melanoma, Lewis lung carcinoma, and human tumor xenograft models in mice.

Continuing studies by Rinehart et al. are directed variously toward providing adequate quantities of these compounds for clinical trials, study of their antitumor mechanism of action, and determination of structure-activity relationships. In addition, the discovery of additional Et compounds, whether minor natural components or precursor compounds, will not only provide evidence for their biosynthetic pathway, but should also be useful for with respect to determining structure-activity relationships.

SUMMARY OF THE INVENTION

The present invention is directed to several newly discovered ecteinascidin (Et) compounds, all isolated from extracts of *Ecteinascidia turbinata*. For a detailed discussion of previously discovered ecteinascidin compounds, as well as the methods used for their isolation and purification, see Sakai et al., *J. Amer. Chem. Soc.*, 1996, 118, 9017, the disclosure of which is hereby incorporated herein by reference.

The structures of the new ecteinascidin compounds reported herein are as follows:

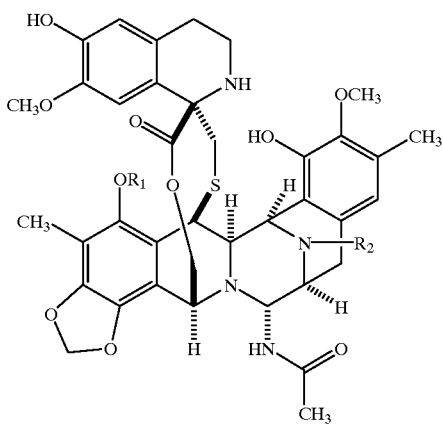

1: ET802, R1 = Ac, R2 = Me
2: ET760, R1 = H, R2 = Me
3: ET788, R1 = Ac, R2 = H

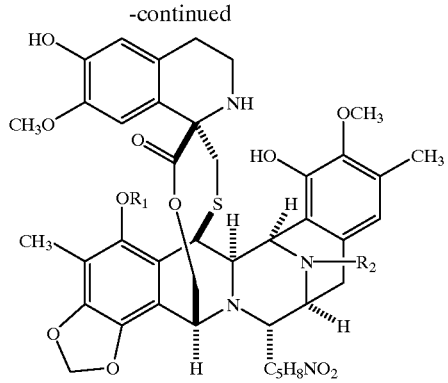

4: ET858, R1 = Ac, R2 = Me

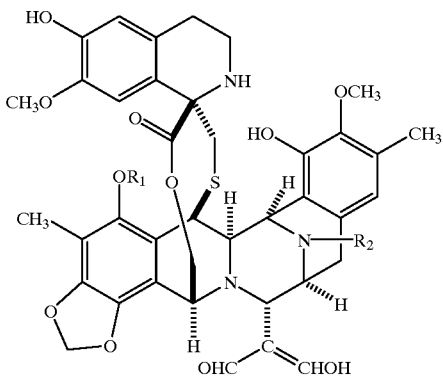

5: ET815, R1 = Ac, R2 = Me

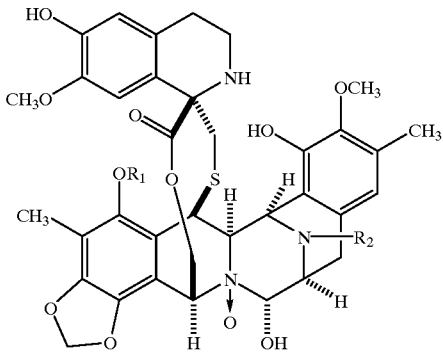

6: ET717, R1 = H, R2 = Me

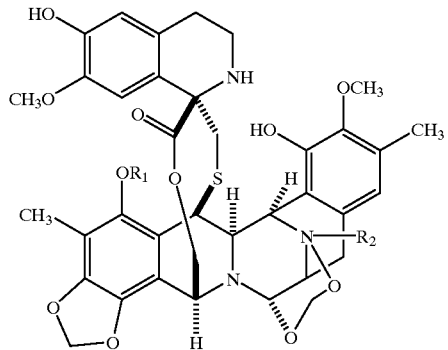

7: ET776, R1 = Ac, R2 = H
8: ET789, R1 = Ac, R2 = Me
(fragment ET757)

-continued

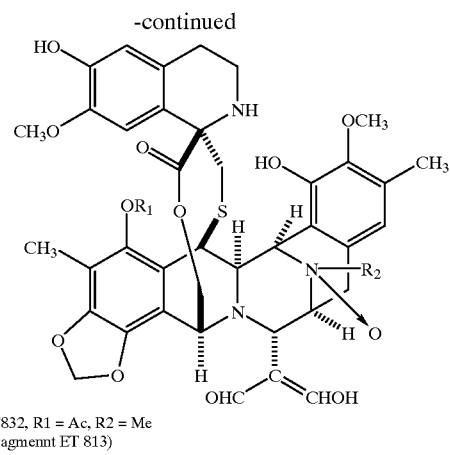

9: ET832, R1 = Ac, R2 = Me
(fragmennt ET 813)

DETAILED DESCRIPTION OF THE INVENTION

Figure 1:
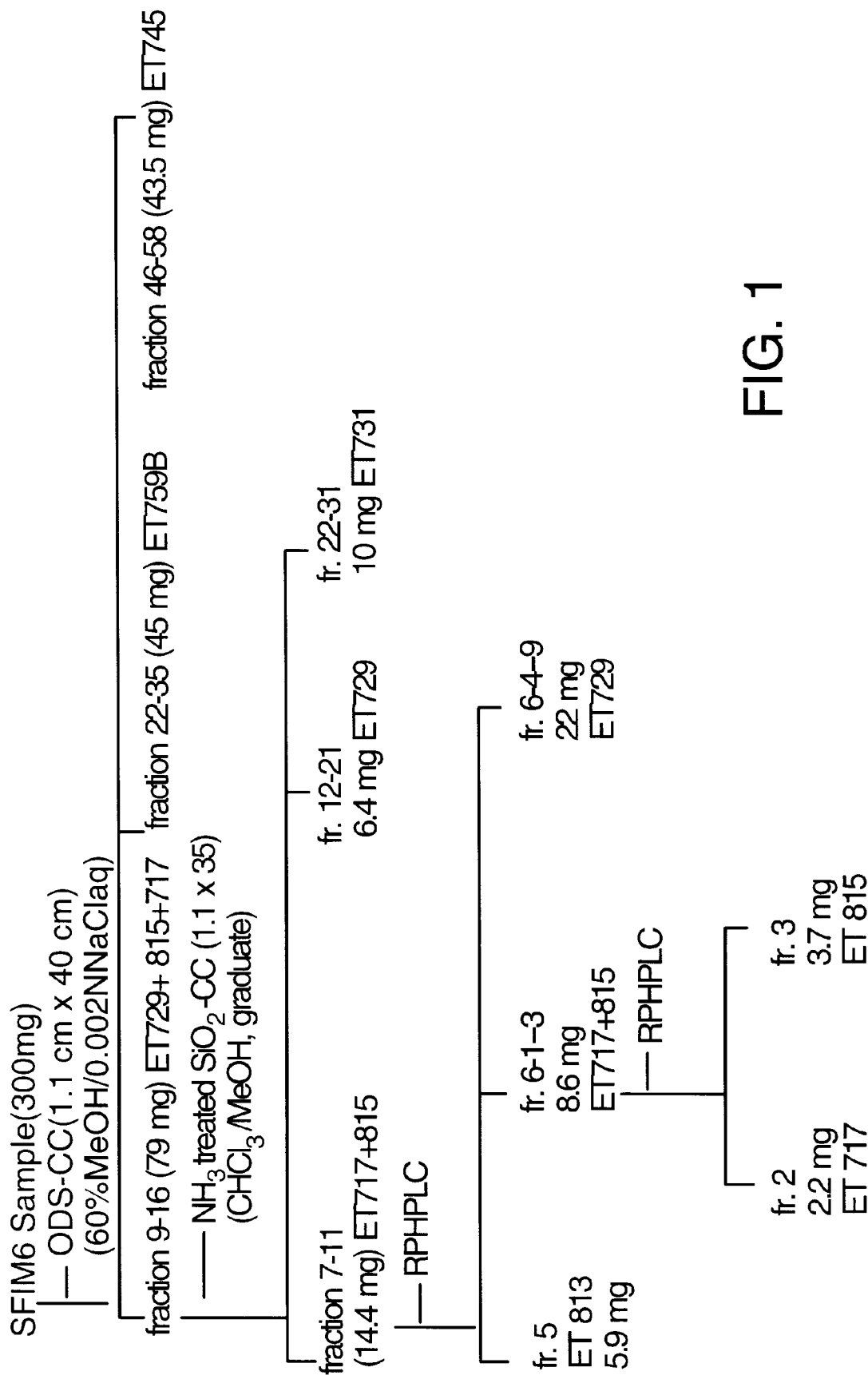
FIG. 1 illustrates schematically the chromatographic processes used to isolate Et 717, Et 815, Et 813, Et 729 and Et 731 from extracts of *Ecteiniascidia turbinata*.
Figure 2:
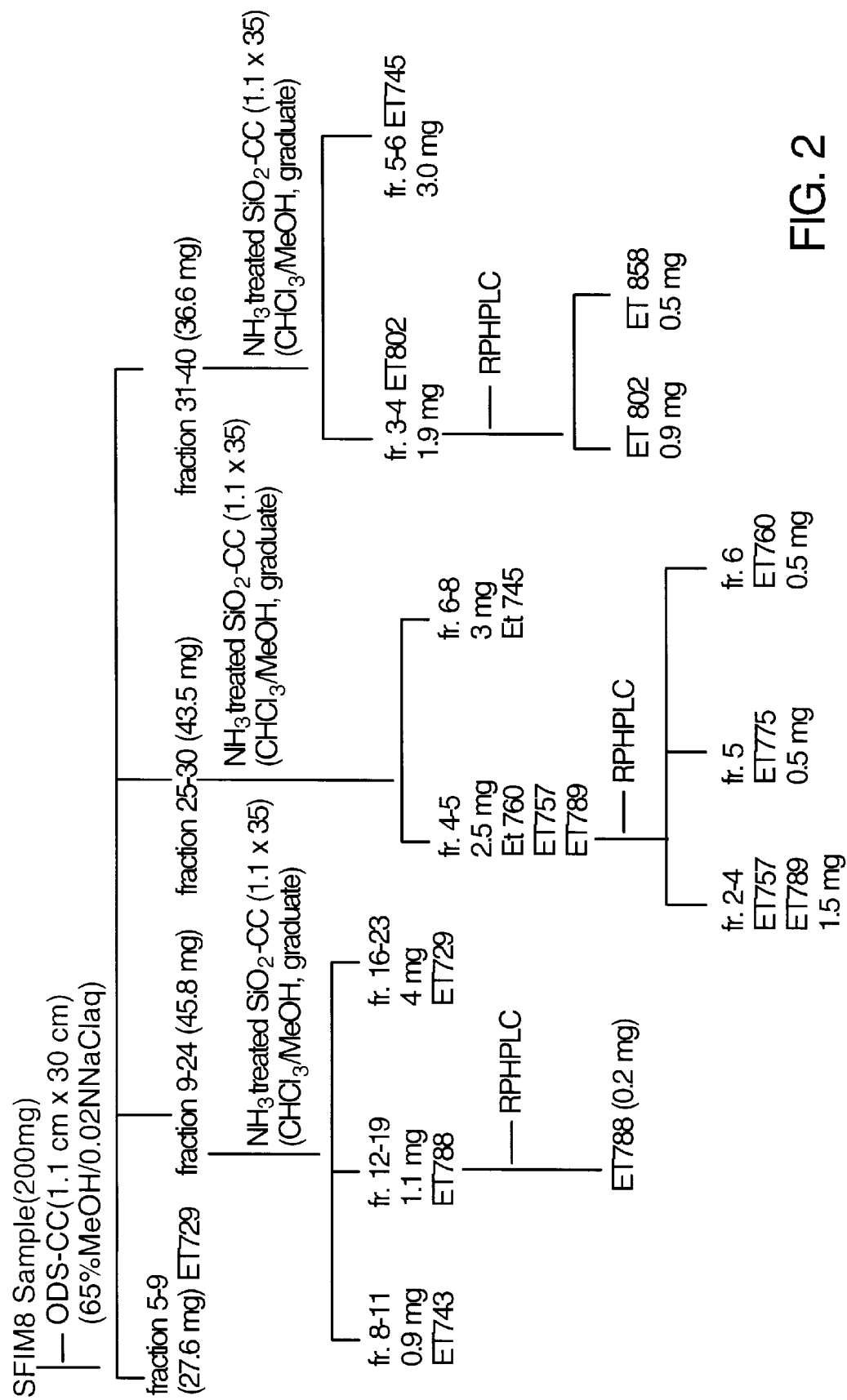
FIG. 2 illustrates schematically the chromatographic processes used to isolate Et 729, Et 743, Et 788, Et 757, Et 789, Et 775, Et 745, Et 760, Et 802, Et 858 and Et 745 from extracts of *Ecteinascidia turbinata*.
Figure 3:
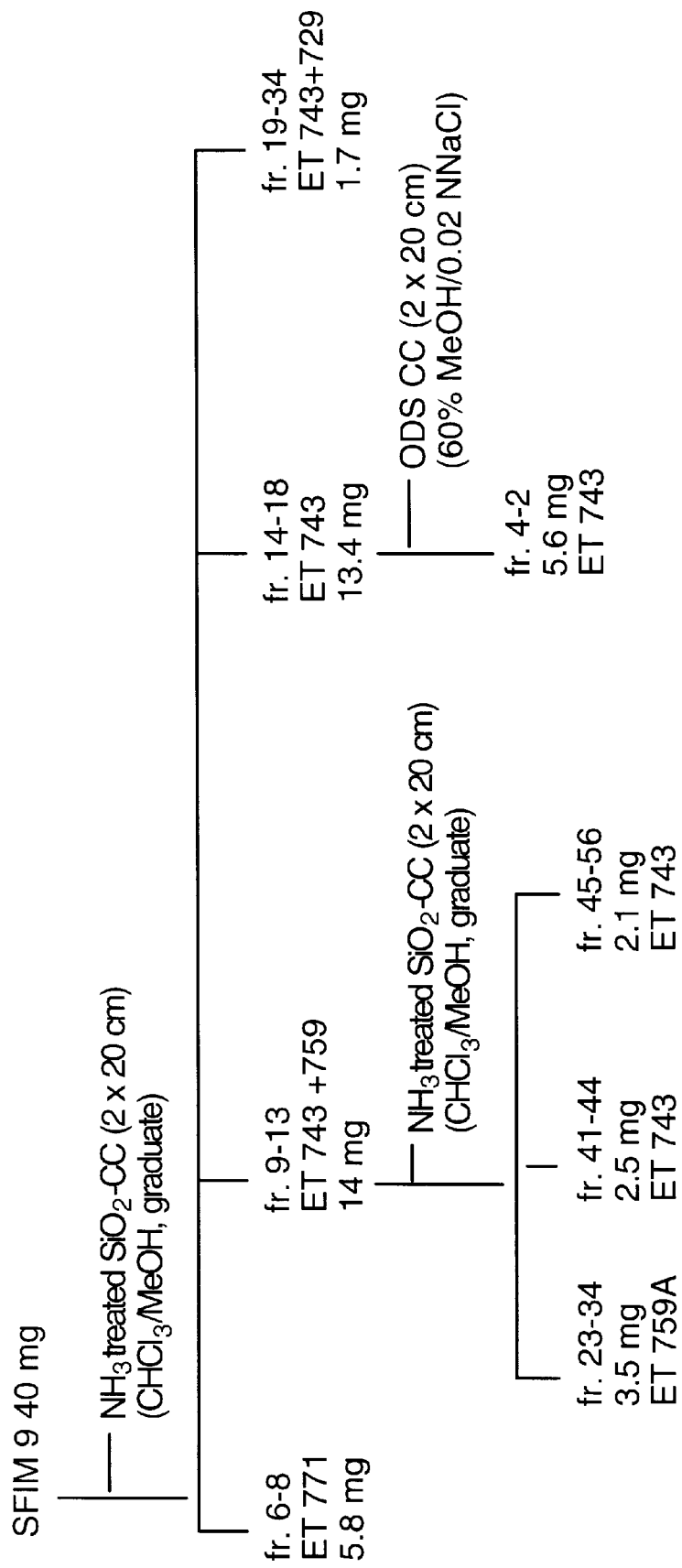
FIG. 3 illustrates schematically the chromatographic processes used to isolate Et 771, Et 759A, Et 743 and Et 729 from extracts of *Ecteinascidia turbinata*.
Figure 4:
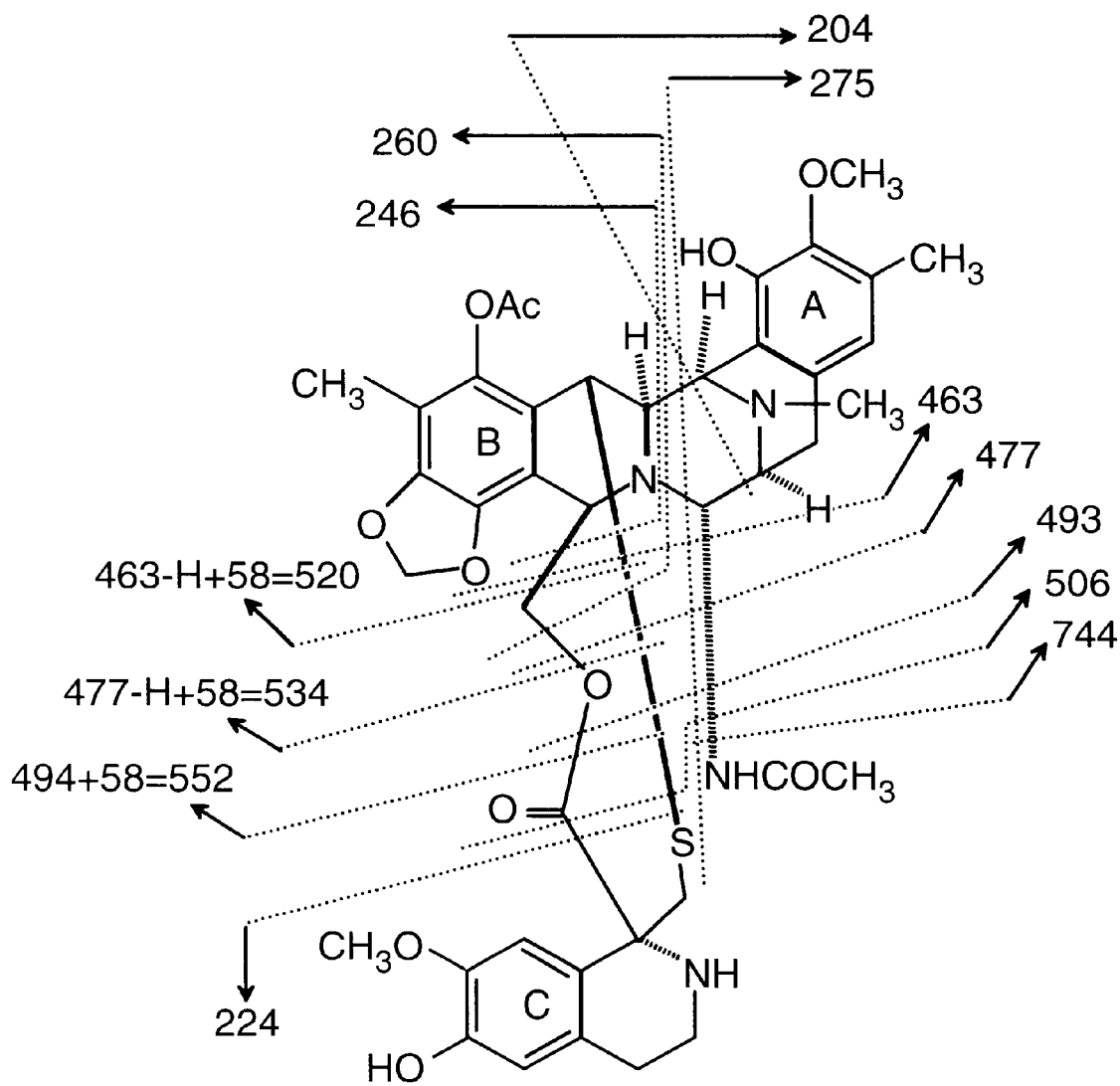
FIG. 4 illustrates the MS/MS fragmentation of Et 802.
Figure 5:
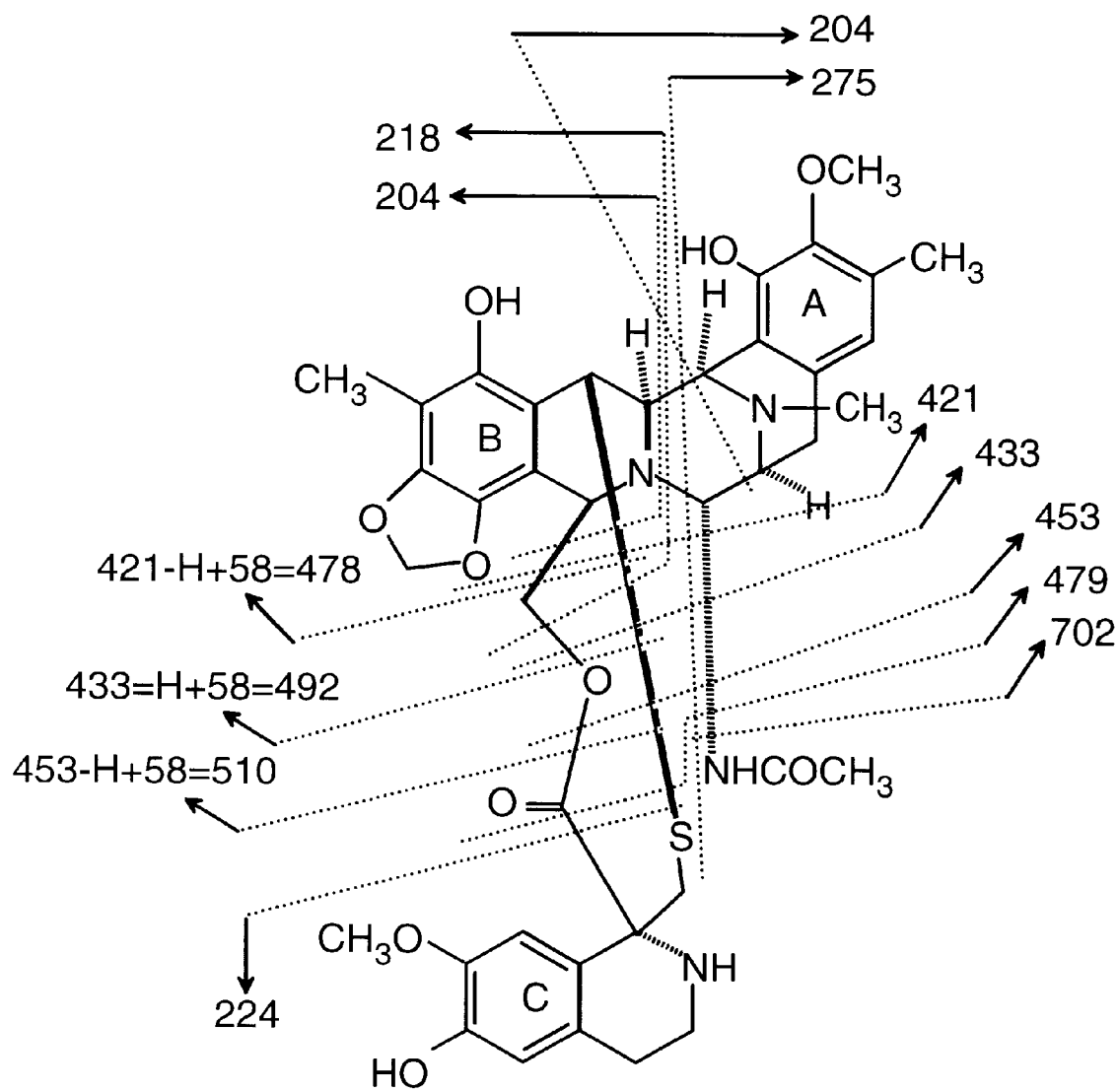
FIG. 5 illustrates the MS/MS fragmentation of Et 760.
Figure 6:
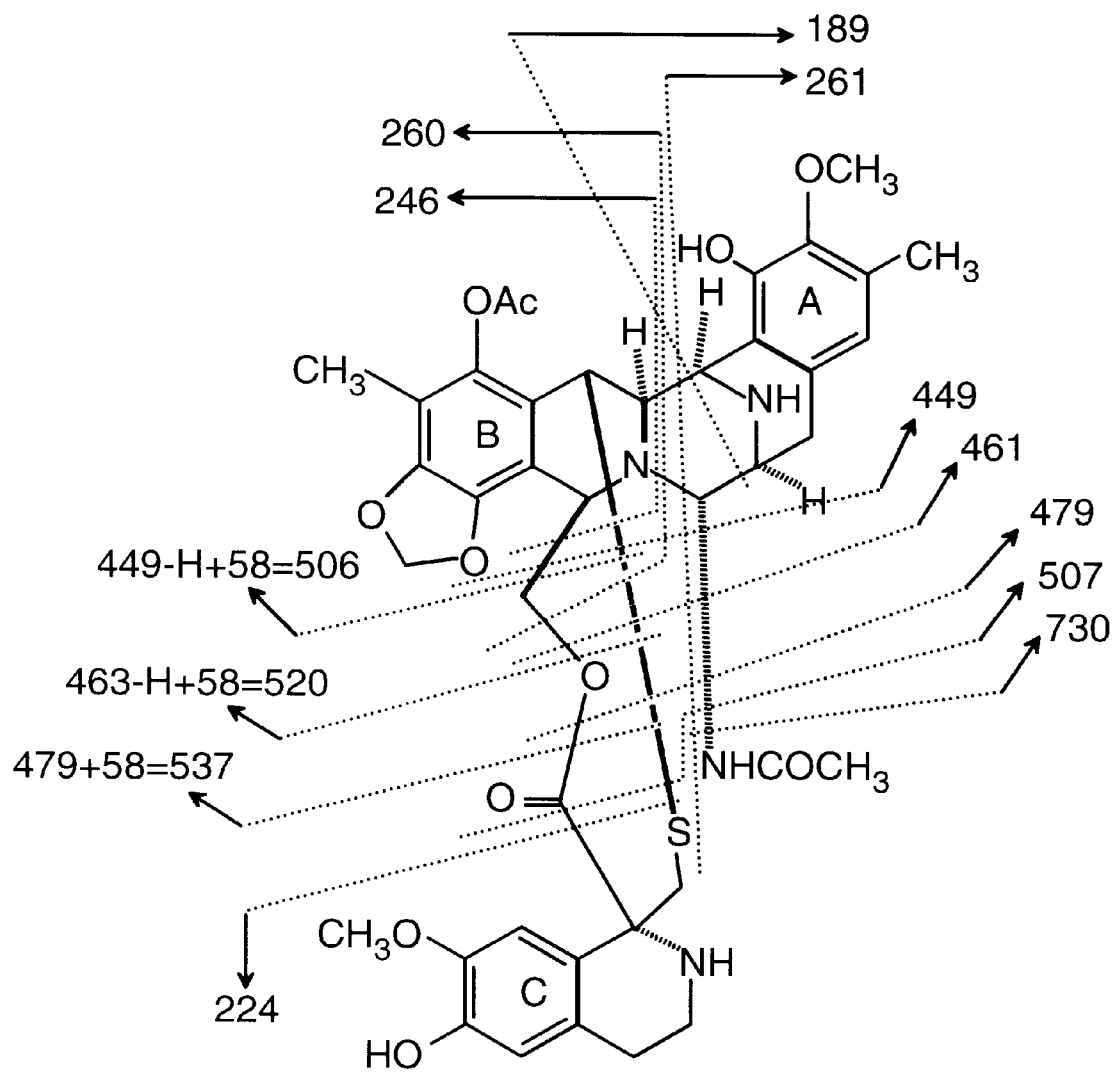
FIG. 6 illustrates the MS/MS fragmentation of Et 788.
Figure 7B:
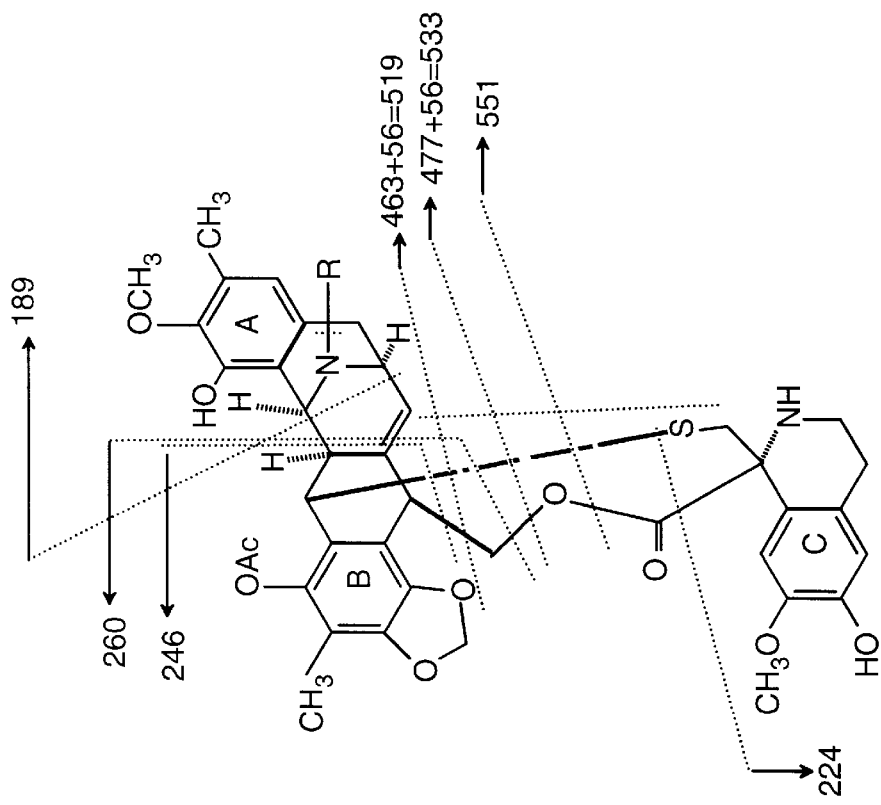
FIG. 7A illustrates the MS/MS fragmentation of Et 858 and FIG. 7B illustrates the MS/MS fragmentation of the fragment ion (m/z 800) thereof.
Figure 7A:
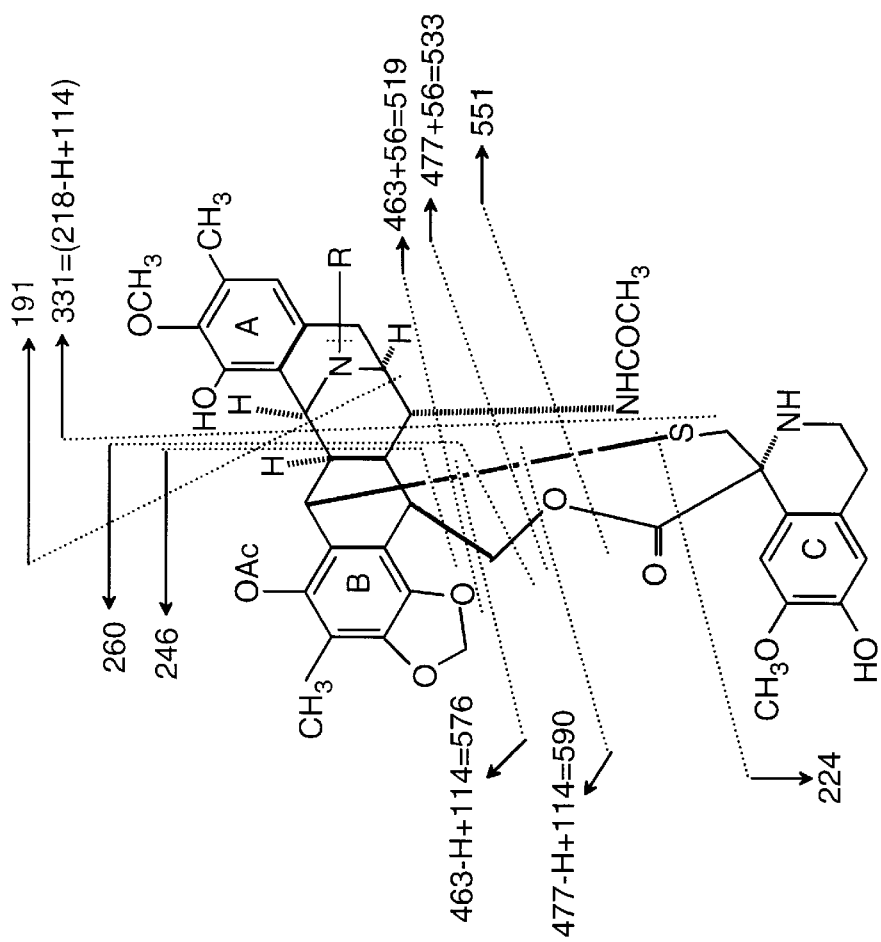
Figure 8:
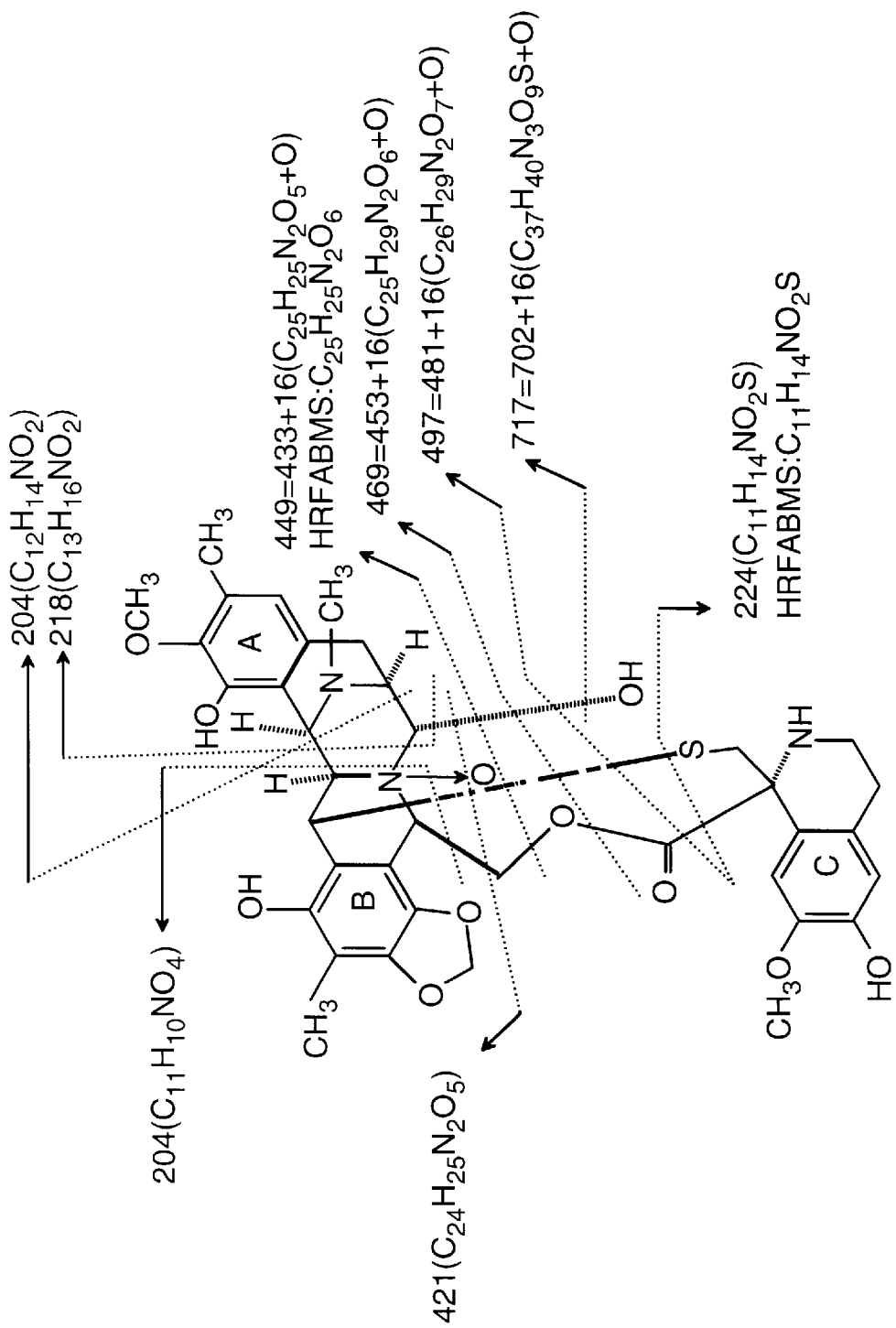
FIG. 8 illustrates the MS/MS fragmentation of Et 717.
Figure 9B:
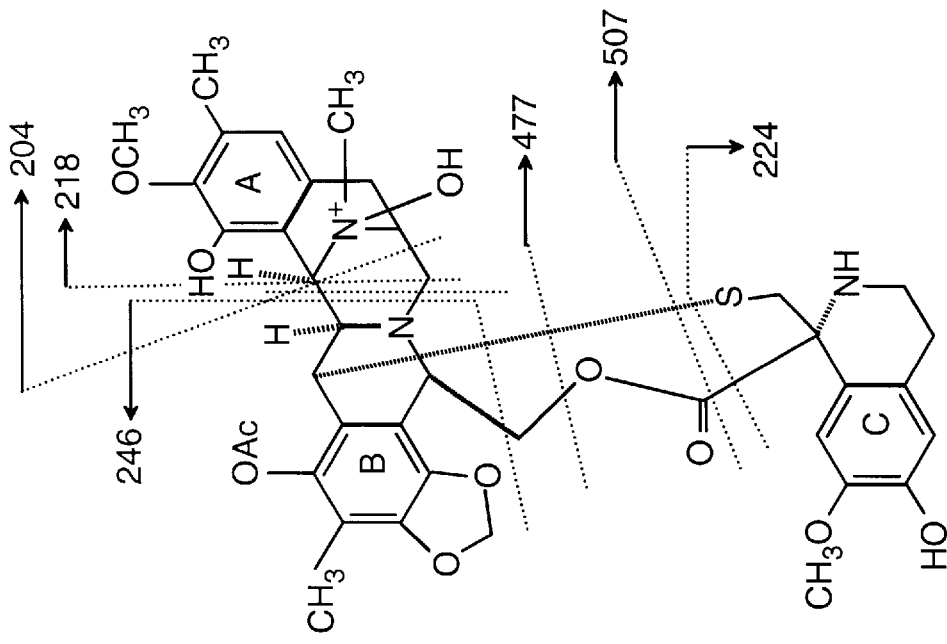
FIG. 9B illustrates the MS/MS fragmentation of the reaction product of Et 789 treated with oxalic acid.
Figure 9A:
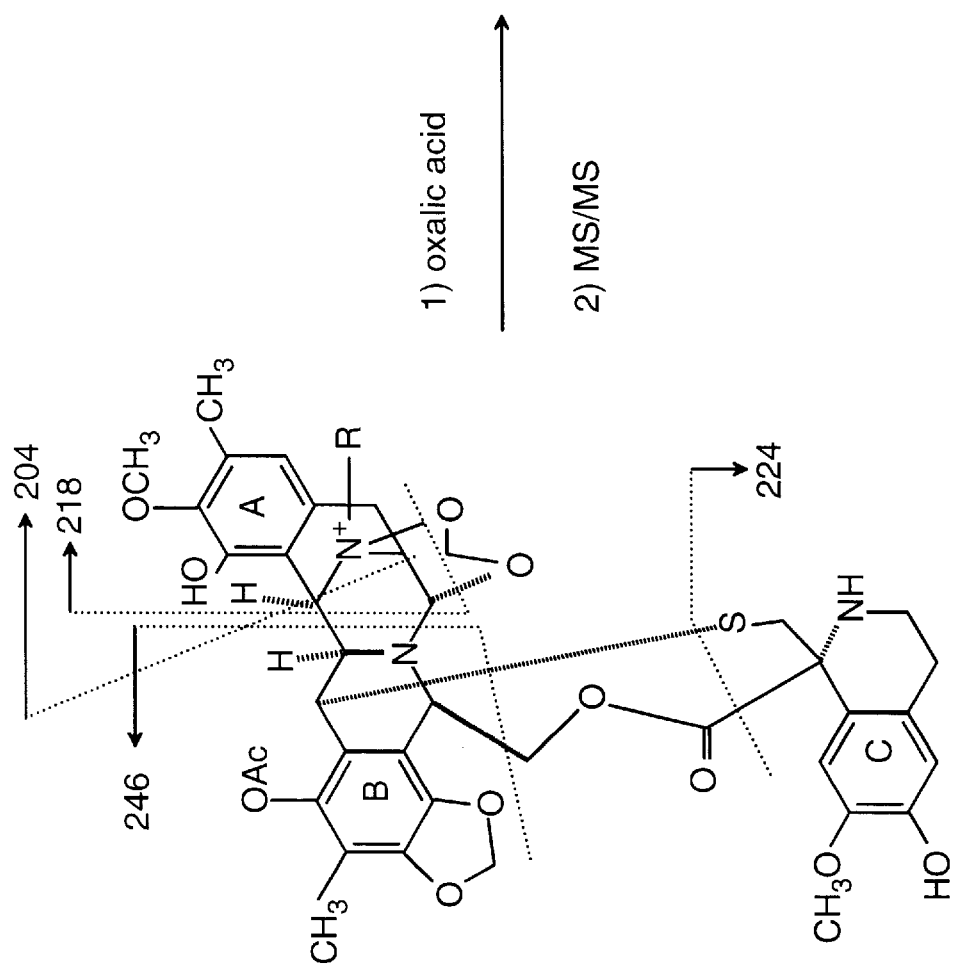
FIG. 9A illustrates the MS/MS fragmentation of Et 789 (8, R=CH$_3$) and Et 775 (7, R=H)

The five new nucleophile substituted ecteinascidin compounds, designated herein is Et 802 (1), Et 788 (2), 760 (3), Et 858 (4), Et 815 (5) and three new N-oxide ecteinascidins, designated herein as Et 717 (6), Et 775 (7) and Et 789 (8) were isolated and purified from extracts of *Ecteinascidia turbinata* by CCC, NP and RP column chromatography and RP-C18 HPLC as described in FIGS. 1–3. These steps provide compounds which are referred to herein as being "substantially pure."

The structures of the new Et compounds were assigned based on mass spectral data (HRFABMS, MS/MS fragmentation) and detailed analysis of 1D and 2D-NMR spectral data. FIGS. 4–9 illustrate MS/MS fragmentation for Et 802, Et 760, Et 788, Et 858, Et 717 and Et 789, respectively.

Spectral data for some of the new ecteinasciding compounds include the following:

Et 802 (1): HRFABMS: m/z 803.2962, M+H ion, $C_{41}H_{47}N_4O_{11}S$, Δ=3.1 mDa; $^1$H NMR, δ 4.15 (d, 1, H-1), 3.45 (br.d, H-3), 4.50 (br, H-4), 4.19 (dd, 1,2, H 11), 3.09 (d, 12, H13), 2.98 (d, 15, H14a), 2.81 (dd, 12, 15, H14b), 6.46 (s, H15), 5.08 (dd, 2, 8, H21), 5.24 (d, 11, H22a), 4.01 (dd, 1, 11, H22b), 3.18 (ddd, H3'a), 2.78 (ddd, H3'b), 2.58 (ddd, H4'a), 2.30 (ddd, H4'b), 6.46 (s, H5'), 6.36 (s, H8'), 2.24 (d, 12, H12'a), 1.93 (d, 12, H12'b), 6.09 (s, —OCH$_2$O—), 6.03 (s, —OCH$_2$O—), 3.52 (s, 7'OMe), 3.66 (s, 17OMe), 2.25 (s, AcMe), 2.07 (s, NMe), 2.24 (s, 16Me), 1.96 (s, 6Me), 2.03 (s, NHCOMe).

Et 788 (2): HRFABMS: m/z 789.2806, M+H ion, $C_{40}H_{45}N_4O_{11}S$, Δ=1.0 mDa; $^1$H NMR, δ 4.21 (d, 1, H-1), 3.45 (br.d, H-3), 4.50 (br, H-4), 4.24 (dd, 1,2, H11), 3.09 (d, 12, H13), 6.48 (s, H15), 5.11 (dd, 2, 8, H21), 5.30 (d, 11, H22a), 4.01 (dd, 1, 11, H22b), 6.48 (s, H5'), 6.39 (s, H8'), 6.13 (s, —OCH$_2$O—), 6.07 (s, —OCH$_2$O—), 3.56 (s, 7'OMe), 3.67 (s, 17OMe), 2.25 (s, AcMe), 2.24 (s, 16Me), 1.96 (s, 6Me), 2.03 (s, NHCOMe).

Et 760 (3): HRFABMS: m/z 761.2856, M+H ion, $C_{39}H_{45}N_4O_{10}S$, Δ=0.2 mDa; $^1$H NMR, δ 4.15 (d, 1, H-1), 3.56 (br.d, H-3), 4.50 (br, H-4), 4.32 (dd, 1,2, H 11), 3.09 (d, 12, H13), 3.00 (d, 15, H14a), 2.86 (dd, 12, 15, H14b), 6.52 (s, H15), 5.11 (dd, 2, 8, H21), 5.20 (d, 11, H22a), 4.01 (dd, 1, 11, H22b), 3.18 (ddd, H3'a), 2.78 (ddd, H3'b), 2.58 (ddd, H4'a), 2.30 (ddd, H4'b), 6.38 (s, H5), 6.34 (s, H8'), 2.24 (d, 12, H12'a), 2.03 (d, 12, H12'b), 5.98 (s, —OCH$_2$O—), 5.85 (s, —OCH$_2$O—), 3.54 (s, 7'OMe), 3.74 (s, 17OMe), 2.13 (s, NMe), 2.29 (s, 16Me), 2.06 (s, 6Me), 2.12 (s, NHCOMe).

Et 858 (4): HRFABMS: m/z 859.3192, M+H ion, $C_{44}H_{51}N_4O_{12}S$, Δ=3.2 mDa; fragment ion m/z 800: m/z 800.2825, M+H ion, $C_{42}H_{46}N_3O_{11}S$, Δ=2.8 mDa; Et 858, $^1$H NMR, δ 4.13 (br.s, H-1), 3.41 (br.d, H-3), 4.50 (br, H-4), 4.36 (d, 3, H11), 2.79 (d, 13, H13), 3.01 (d, 12, H14a), 2.88 (dd, 12, 13, H14b), 6.50 (s, H15), 5.10 (d, 2, H21), 5.28 (d, 11, H22a), 4.09 (dd, 1.5, 11, H22b), 3.18 (ddd, H3'a), 2.62 (ddd, H3'b), 2.53 (ddd, H4'a), 2.45 (ddd, H4'b), 6.43 (s, H5'), 6.38 (s, H8'), 2.25 (d, 12, H12'a), 2.14 (d, 12, H12'b), 6.08 (s, —OCH$_2$O—), 5.98 (s, —OCH$_2$O—), 3.57 (s, 7'OMe), 3.73 (s, 17OMe), 2.28 (s, AcMe), 2.27 (s, 16Me), 2.01 (s, 6Me), 2.15 (s, NHCOMe), 2.09 (s, NHCOMe), 3.25 (NHCOMe), 2.64 (m, NHCOMe).

Et 717 (6): HRFABMS: m/z 718.2435, M+H ion, $C_{37}H_{40}N_3O_{10}S$, Δ=-0.1 mDa; $^1$H NMR, δ 6.55 (H15), 6.44 (H8'), 6.38 (H5'), 6.07, 5.92 (—OCH$_2$O—), 5.78, 4.09 (H22a,b), 5.30 (H1), 5.19 (H21), 4.92 (H4), 4.57 (H11), 4.41 (H3), 3.64 (H13), 3.22, 2.91 (H14a,b), 3.00, 2.85 (H3'a,b), 2.61, 2.38 (H4'a,b), 3.74 (17—OCH$_3$), 3.54 (7'—OCH$_3$), 2.35 (6—CH$_3$), 2.27 (16—CH$_3$), 2.16 (N—CH$_3$).

Et 775 (7): HRFABMS: m/z 776, $C_{39}H_{42}N_3O_{12}S$, Δ=-0.0 mDa.

Et 789 (8): HRFABMS: m/z 790, $C_{40}H_{44}N_3O_{12}S$, Δ=-0.2 mDa; 12N—CH$_3$, δ 2.65 (singlet) observed in $^1$H NMR.

Several of these new ecteinascidin compounds show exceedingly potent cytotoxicity against L1210 (see Table 1).

TABLE 1

| Et Compound | IC$_{50}$ ng/ml against L1210 |
|---|---|
| Et 802 (1) | 7 |
| Et 788 (2) | 0.5 |
| Et 760 (3) | 32 |
| Et 858 (4) | 0.4 |
| Et 815 (5) | 0.4 |

As shown above, the present invention is directed to bioactive compounds. These compounds have been prepared in substantially pure form, i.e., at a purity level sufficient to allow physical and biological characterization thereof. As described above, these compounds have been found to possess specific antitumor activities and as such they will be useful as medicinal agents in mammals, particularly in humans. Thus, another aspect of the present invention concerns pharmaceutical compositions containing the active compounds identified herein and methods of treatment employing such pharmaceutical compositions.

The active compounds of the present invention exhibit antitumor activity. Thus, the present invention also provides a method of treating any mammal affected by a malignant tumor sensitive to these compounds, which comprises administering to the affected individual a therapeutically effective amount of an active compound or mixture of compounds, or pharmaceutical compositions thereof. The present invention also relates to pharmaceutical preparations, which contain as active ingredient one or more of the compounds of this invention, as well as the processes for its preparation.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

The correct dosage of a pharmaceutical composition comprising the compounds of this invention will vary according to the particular formulation, the mode of application, and the particular situs, host and bacteria or tumor being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

Several known ecteinascidin compounds, including Et 743 and Et 729 were also isolated, as shown below in Table 2.

TABLE 2

Quantities of Et Compounds Isolated

| Fraction A (550 mg) | Fraction B (261 mg) | Fraction C (40 mg) |
|---|---|---|
| Et 729 39.4 mg | Et 729 31.6 mg | Et 743 10.2 mg |
| Et 731 11.1 mg | Et 743 0.9 mg | Et 771 5.8 mg |

TABLE 2-continued

Quantities of Et Compounds Isolated

| Fraction A (550 mg) | Fraction B (261 mg) | Fraction C (40 mg) |
|---|---|---|
| Et 745 45.4 mg | Et 745 6.0 mg | Et 759A 3.5 mg |
| Et 759B 46.4 mg | Et 802 (1) 1.4 mg* | |
| Et 597 3.4 mg | Et 788 (2) 0.2 mg* | |
| Et 717 (6) 2.6 mg* | Et 760 (3) 1.0 mg* | |
| Et 815 (5) 5.1 mg* | Et 858 (4) 0.5 mg* | |
| Et 814 (9) 5.9 mg* | Et 789 (8) 1.5 mg* | |
| | Et 775 (7) 0.5 mg* | |

* - New Ecteinascidin Compounds

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. Substantially pure Ecteinascidin 717, free of the cellular debris of *Ecteinascidia turbinata*, said compound having the following structure:

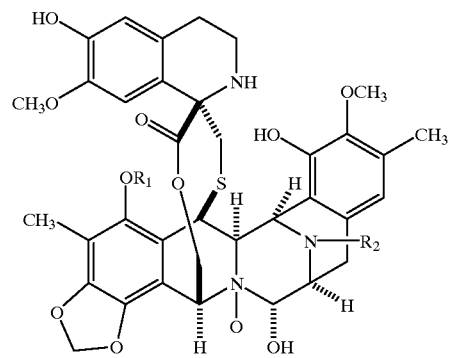

ET717, R1 = H, R2 = Me.

2. Substantially pure Ecteinascidin 815, free of the cellular debris of *Ecteinascidia turbinata*, said compound having the following structure:

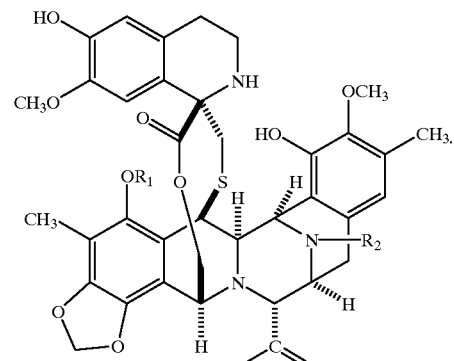

ET815, R1 = Ac, R2 = Me

3. Substantially pure Ecteinascidin 832, free of the cellular debris of *Ecteinascidia turbinata*, said compound having the following structure:

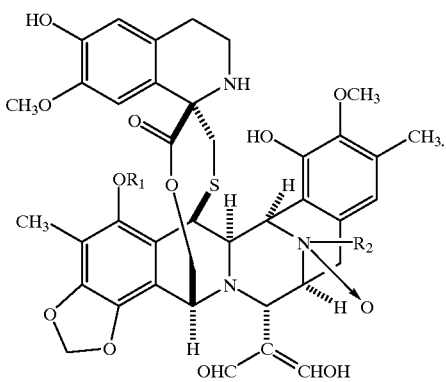

ET832, R1 = Ac, R2 = Me

4. Substantially pure Ecteinascidin 802, free of the cellular debris of *Ecteinascidia turbinata*, said compound having the following structure:

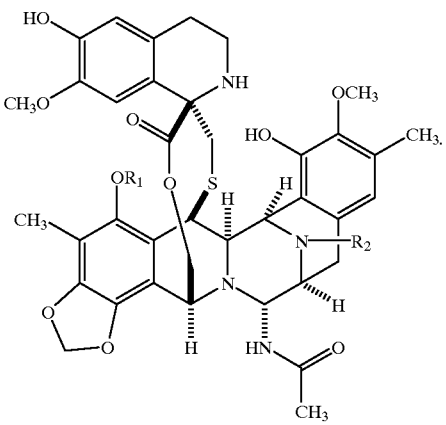

ET802, R1 = Ac, R2 = Me

5. Substantially pure Ecteinascidin 788, free of the cellular debris of *Ecteinascidia turbinata*, said compound having the following structure:

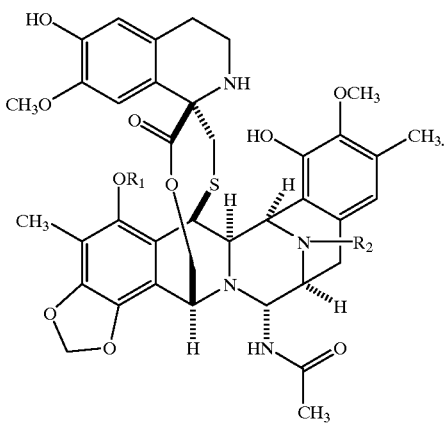

ET788, R1 = Ac, R2 = H

6. Substantially pure Ecteinascidin 760, free of the cellular debris of *Ecteinascidia turbinata*, said compound having the following structure:

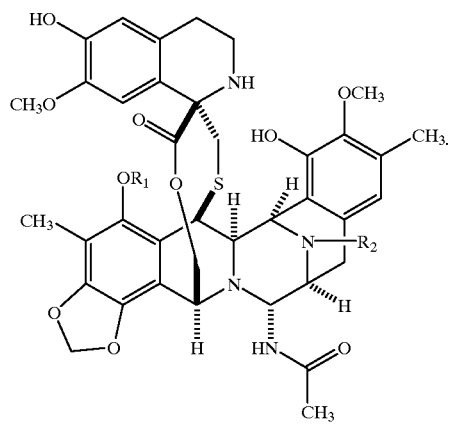

ET760, R1 = H, R2 = Me

7. Substantially pure Ecteinascidin 858, free of the cellular debris of *Ecteinascidia turbinata*, said compound having the following structure:

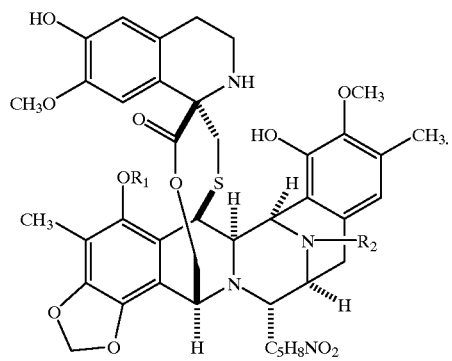

ET858, R1 = Ac, R2 = Me

8. Substantially pure Ecteinascidin 789, free of the cellular debris of *Ecteinascidia turbinata*, said compound having the following structure:

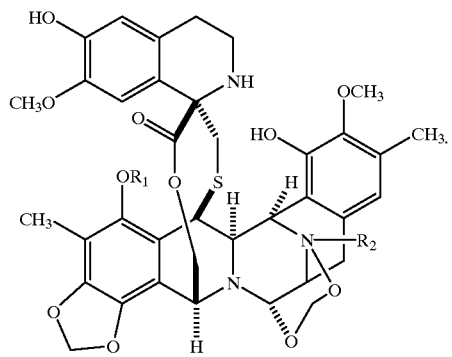

ET789, R1 = Ac, R2 = Me

9. Substantially pure Ecteinascidin 775, free of the cellular debris of *Ecteinascidia turbinata*, said compound having the following structure:

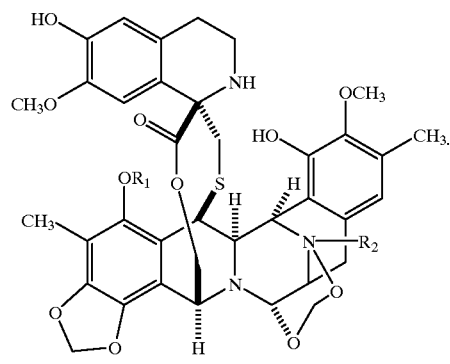

R1 = Ac, R2 = H

10. A pharmaceutical or veterinary composition comprising an effective antitumor amount of the substantially pure compound designated herein as Et 717 and a pharmaceutically acceptable carrier, diluent or excipient, said compound having the following structure:

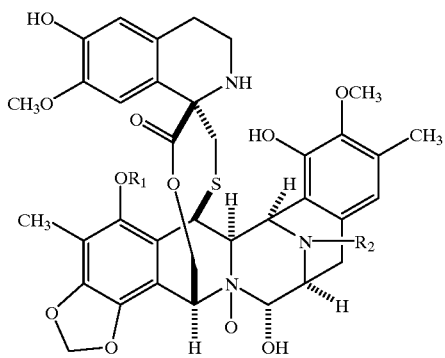

ET717, R1 = H, R2 = Me.

11. A pharmaceutical or veterinary composition comprising an effective antitumor amount of the substantially pure compound designated herein as Et 815 and a pharmaceutically acceptable carrier, diluent or excipient, said compound having the following structure:

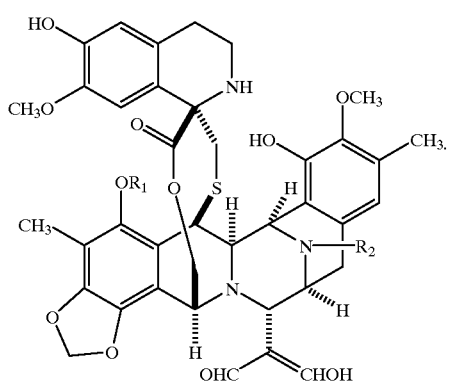

-continued

ET815, R1 = Ac, R2 = Me

12. A pharmaceutical or veterinary composition comprising an effective antitumor amount of the substantially pure compound designated herein as Et 832 and a pharmaceutically acceptable carrier, diluent or excipient, said compound having the following structure:

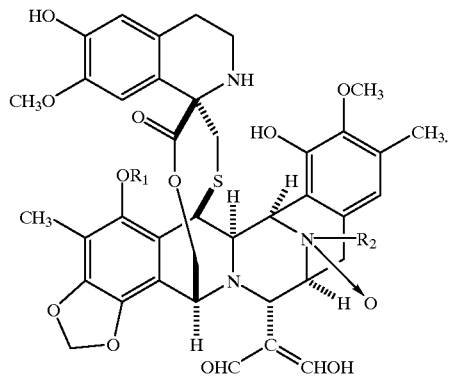

ET832, R1 = Ac, R2 = Me

13. A pharmaceutical or veterinary composition comprising an effective antitumor amount of the substantially pure compound designated herein as Et 802 and a pharmaceutically acceptable carrier, diluent or excipient, said compound having the following structure:

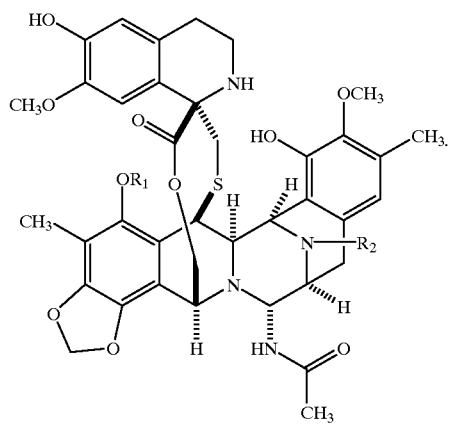

ET802, R1 = Ac, R2 = Me

14. A pharmaceutical or veterinary composition comprising an effective antitumor amount of the substantially pure compound designated herein as Et 788 and a pharmaceutically acceptable carrier, diluent or excipient, said compound having the following structure:

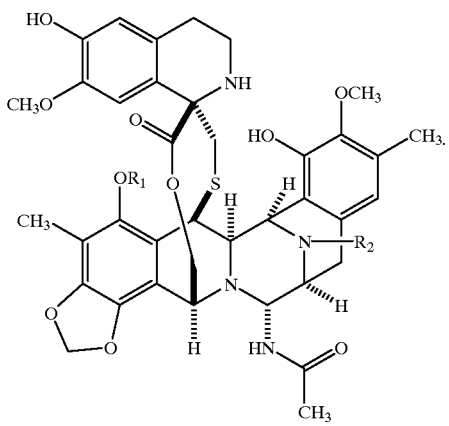

ET788, R1 = Ac, R2 = H

15. A pharmaceutical or veterinary composition comprising an effective antitumor amount of the substantially pure compound designated herein as Et 760 and a phaimaceutically acceptable carrier, diluent or excipient, said compound having the following structure:

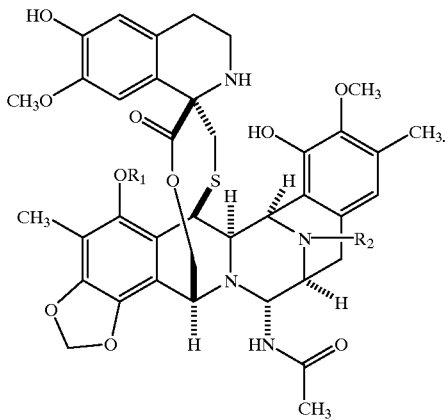

ET760, R1 = H, R2 = Me

16. A pharmaceutical or veterinary composition comprising an effective antitumor amount of the substantially pure compound designated herein as Et 858 and a pharmaceutically acceptable carrier, diluent or excipient, said compound having the following structure:

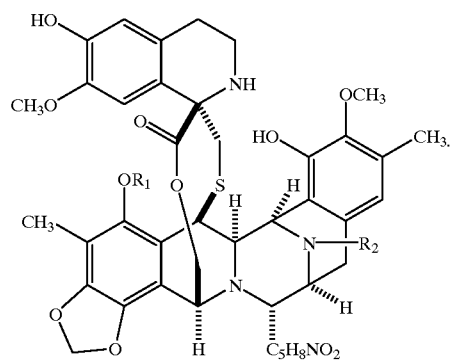

ET858, R1 = Ac, R2 = Me

17. A pharmaceutical or veterinary composition comprising an effective antitumor amount of the substantially pure compound designated herein as Et 789 and a pharmaceutically acceptable carrier, diluent or excipient, said compound having the following structure:

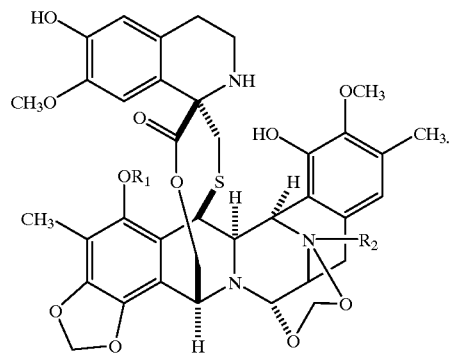

ET789, R1 = Ac, R2 = Me

18. A pharmaceutical or veterinary composition comprising an effective antitumor amount of the substantially pure compound designated herein as Et 775 and a pharmaceutically acceptable carrier, diluent or excipient, said compound having the following structure:

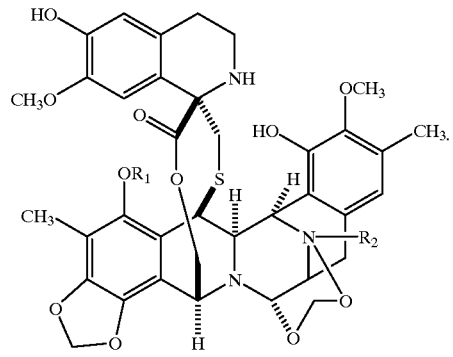

R1 = Ac, R2 = H

19. A method of treating a patient suffering from a mammalian tumor comprising administering to said patient, an effective antitumor amount of the substantially pure compound designated herein as Et 717 and a pharmaceutically acceptable carrier, diluent or excipient, said compound having the following structure:

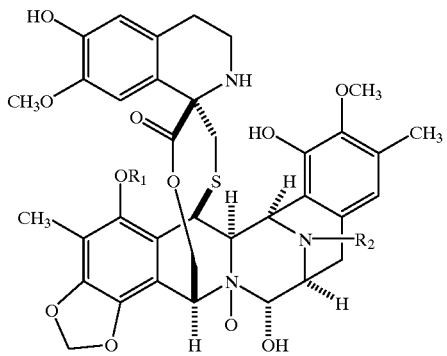

ET717, R1 = H, R2 = Me.

20. A method of treating a patient suffering from a mammalian tumor comprising administering to said patient, an effective antitumor amount of the substantially pure compound designated herein as Et 815 and a pharmaceutically acceptable carrier, diluent or excipient, said compound having the following structure:

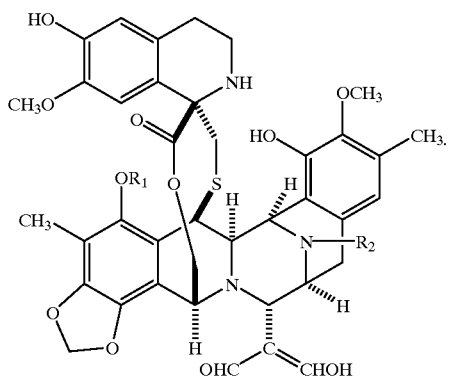

ET815, R1 = Ac, R2 = Me

21. A method of treating a patient suffering from a mammalian tumor comprising administering to said patient, an effective antitumor amount of the substantially pure compound designated herein as Et 832 and a pharmaceutically acceptable carrier, diluent or excipient, said compound having the following structure:

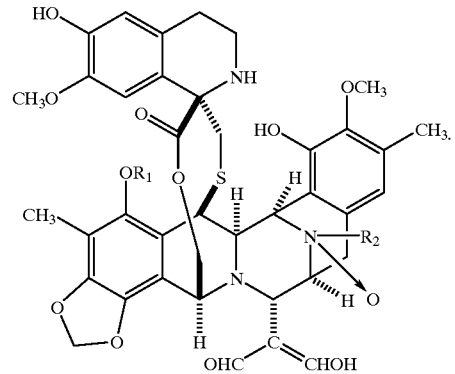

ET832, R1 = Ac, R2 = Me

22. A method of treating a patient suffering from a mammalian tumor comprising administering to said patient, an effective antitumor amount of the substantially pure compound designated herein as Et 802 and a pharmaceutically acceptable carrier, diluent or excipient, said compound having the following structure:

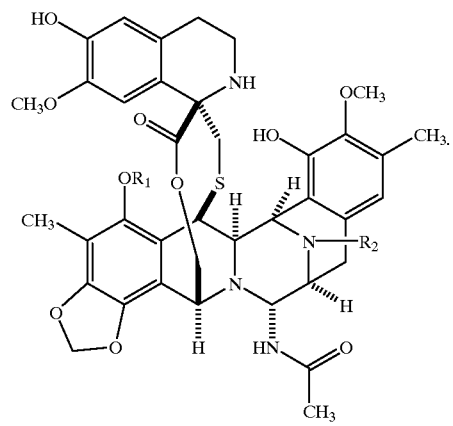

ET802, R1 = Ac, R2 = Me

23. A method of treating a patient suffering from a mammalian tumor comprising administering to said patient, an effective antitumor amount of the substantially pure compound designated herein as Et 788 and a pharmaceutically acceptable carrier, diluent or excipient, said compound having the following structure:

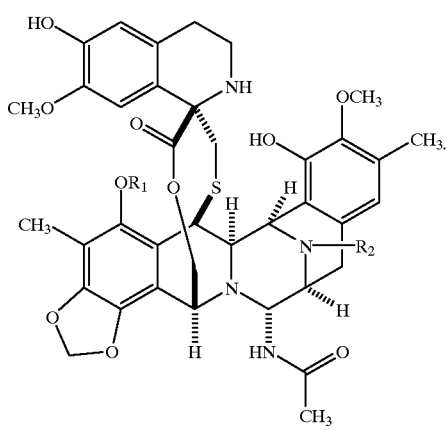

ET788, R1 = Ac, R2 = H

24. A method of treating a patient suffering from a mammalian tumor comprising administering to said patient, an effective antitumor amount of the substantially pure compound designated herein as Et 760 and a pharmaceutically acceptable carrier, diluent or excipient, said compound having the following structure:

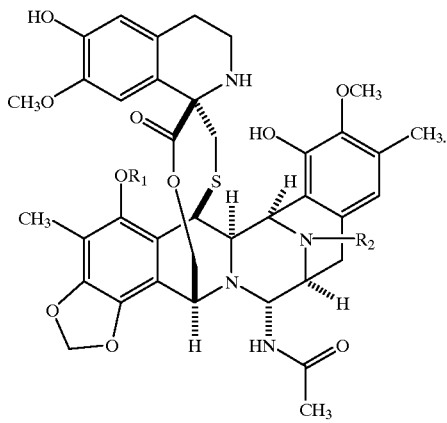

ET760, R1 = Ac, R2 = Me

25. A method of treating a patient suffering from a mammalian tumor comprising administering to said patient, an effective antitumor amount of the substantially pure compound designated herein as Et 858 and a pharmaceutically acceptable carrier, diluent or excipient, said compound having the following structure:

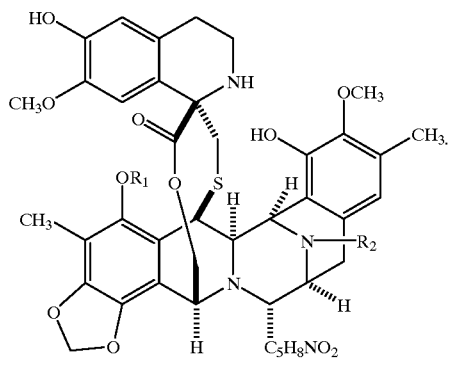

ET858, R1 = Ac, R2 = Me

26. A method of treating a patient suffering from a mammalian tumor comprising administering to said patient, an effective antitumor amount of the substantially pure compound designated herein as Et 789 and a pharmaceutically acceptable carrier, diluent or excipient, said compound having the following structure:

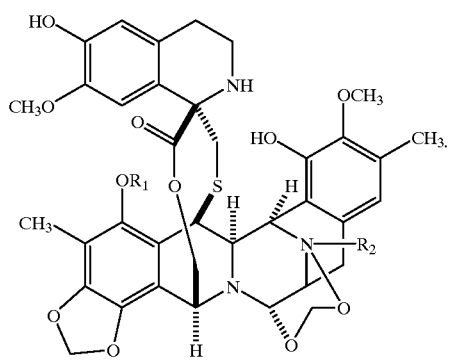

ET789, R1 = Ac, R2 = Me

27. A method of treating a patient suffering from a mammalian tumor comprising administering to said patient, an effective antitumor amount of the substantially pure compound designated herein as Et 775 and a pharmaceutically acceptable carrier, diluent or excipient, said compound having the following structure:

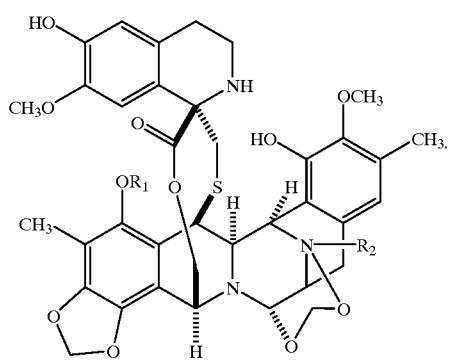

R1 = Ac, R2 = H

* * * * *